United States Patent [19]

Crocco et al.

[11] Patent Number: 5,166,372
[45] Date of Patent: Nov. 24, 1992

[54] EPOXIDATION PROCESS

[75] Inventors: Guy L. Crocco, Wilmington, Del.; Wilfred F. Shum, West Chester, Pa.; John G. Zajacek, Devon, Pa.; Haven S. Kesling, Jr., Drexel Hill, Pa.

[73] Assignee: Arco Chemical Technology, L.P., Wilmington, Del.

[21] Appl. No.: 832,568

[22] Filed: Feb. 7, 1992

[51] Int. Cl.$^5$ ............... C07D 301/12; C07D 303/04
[52] U.S. Cl. .................. 549/531; 568/814; 568/860
[58] Field of Search ........................ 549/531

[56] References Cited

U.S. PATENT DOCUMENTS

| | | | |
|---|---|---|---|
| 2,819,949 | 1/1959 | Keeler et al. | 23/207 |
| 2,869,989 | 1/1959 | Keeler et al. | 23/207 |
| 2,871,102 | 1/1959 | Rust et al. | 23/207 |
| 2,871,103 | 1/1959 | Skinner et al. | 23/207 |
| 2,871,104 | 1/1959 | Rust | 23/207 |
| 2,949,343 | 8/1960 | Hood et al. | 23/207 |
| 3,003,853 | 10/1961 | Mecorney et al. | 23/207 |
| 3,012,860 | 12/1961 | Meeker et al. | 23/207 |
| 3,074,782 | 1/1963 | Meeker et al. | 23/207 |
| 3,778,451 | 12/1973 | Poite | 549/531 |
| 4,303,632 | 12/1981 | Gosser | 423/591 |
| 4,864,041 | 9/1989 | Hill | 549/531 |
| 4,897,252 | 1/1990 | Cochran et al. | 423/591 |
| 4,973,718 | 11/1990 | Buchler et al. | 549/531 |
| 4,975,266 | 12/1990 | Albal et al. | 423/591 |
| 4,987,226 | 1/1991 | Buchler et al. | 549/531 |
| 5,039,508 | 8/1991 | Cochran et al. | 423/591 |
| 5,041,680 | 8/1991 | Albal et al. | 568/311 |

FOREIGN PATENT DOCUMENTS

| | | |
|---|---|---|
| 3841733 | 12/1988 | Fed. Rep. of Germany . |
| 3902357 | 8/1990 | Fed. Rep. of Germany . |
| 1505332 | 12/1967 | France . |
| 758907 | 10/1956 | United Kingdom . |
| 758967 | 10/1956 | United Kingdom . |

OTHER PUBLICATIONS

Herrmann, *J. Organomet. Chem.*, 382, 1 (1990).
Herrmann, et al., *Angew. Chem.*, 100, 394 (1988); a copy of *Angew. Chem. Int. Ed. Eng.* 27, 396 (1988).

*Primary Examiner*—Joseph E. Evans
*Attorney, Agent, or Firm*—Stephen D. Harper

[57] ABSTRACT

Olefins are epoxidized by hydrogen peroxide in the presence of an organorhenium oxide catalyst and an alkyl aryl secondary alcohol solvent. High yields of epoxides with minimal non-selective loss of either hydrogen peroxide or olefin are realized. The epoxidation may comprise one step of an integrated process wherein an oxidant mixture is generated by molecular oxygen oxidation of the alkyl aryl secondary alcohol and used directly in the epoxidation without further purification or extraction.

29 Claims, 1 Drawing Sheet

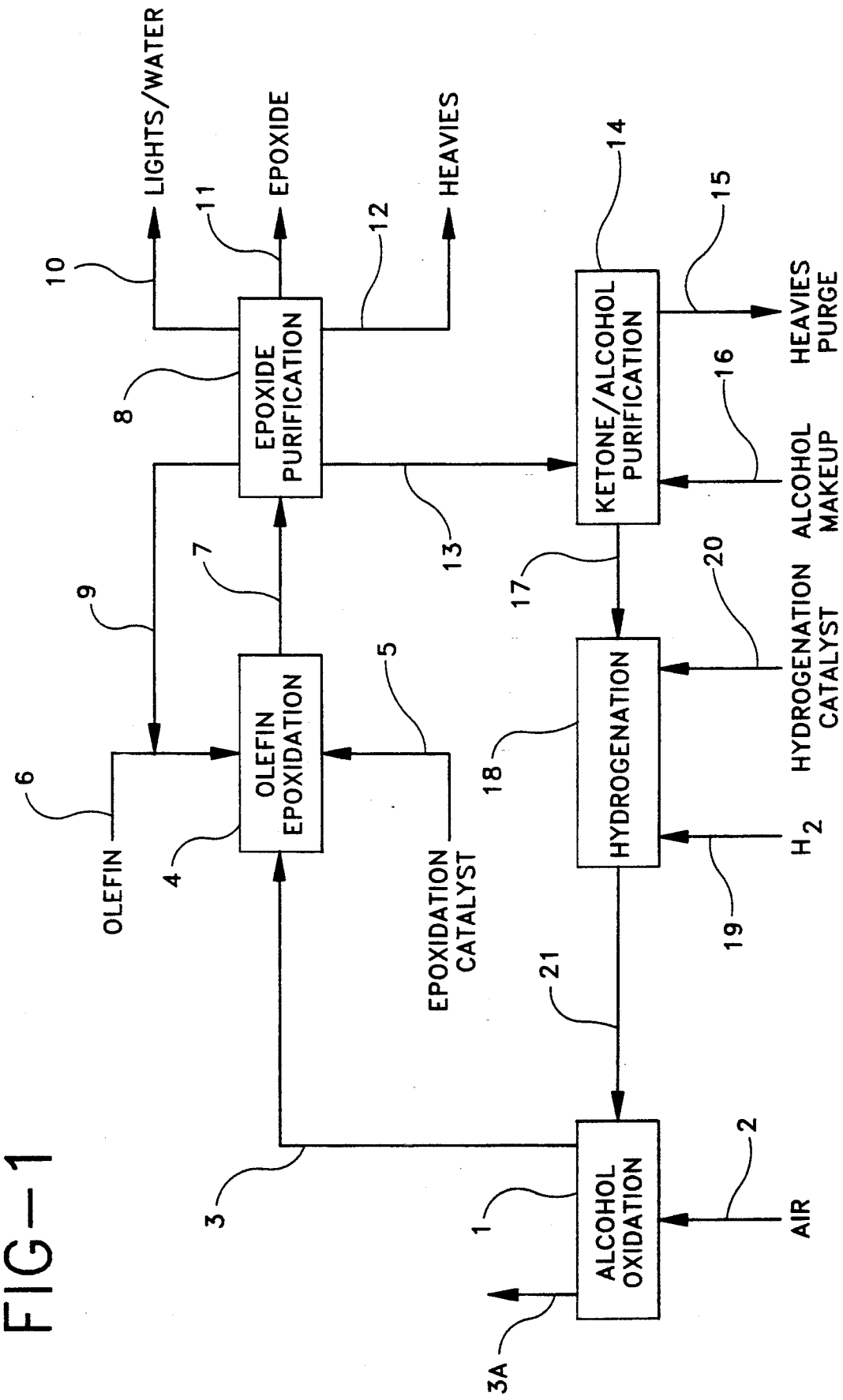

EPOXIDATION PROCESS

FIELD OF THE INVENTION

This invention relates to methods of epoxidizing olefins so as to obtain products containing epoxide functional groups. In particular, the invention pertains to processes whereby hydrogen peroxide is reacted with an ethylenically unsaturated substrate in a reaction medium containing an alkyl aryl secondary alcohol solvent and an organorhenium oxide catalyst to yield an oxirane. An oxidant solution comprised of the alcohol and the hydrogen peroxide generated by reaction of the alcohol with molecular oxygen may be employed in the process of this invention.

BACKGROUND OF THE INVENTION

Epoxides such as ethylene oxide, propylene oxide, 1,2-butene oxide and the like are useful intermediates for the preparation of a wide variety of products. The oxirane functionality in such compounds is highly reactive and may be ring-opened with any number of nucleophilic reactants. For example, epoxides may be hydrolyzed to yield glycols useful as anti-freeze components, food additives, or reactive monomers for the preparation of condensation polymers such as polyesters.

Polyether polyols generated by the ring-opening polymerization of epoxides are widely utilized as intermediates in the preparation of polyurethane foams, elastomers, sealants, coatings, and the like. The reaction of epoxides with alcohols provides glycol ethers, which may be used as polar solvents in a number of applications.

Many different methods for the preparation of epoxides have been developed. One such method involves the use of certain organorhenium oxide compounds to catalyze olefin oxidation by hydrogen peroxide. This method is described, for example, in German Patent No. 3,902,357 and Herrmann, J. Organomet. Chem. 382, 1(1990). While high yields of certain epoxides may be obtained by this procedure, attempts to prepare other epoxides were much less successful. In particular, these publications teach that a 1,2-diol by-product is often produced in addition to or instead of the desired epoxide. The formation of such by-products is especially favored, according to the prior art, when the reaction temperature exceeds 10° C. Maintaining an epoxidation reaction mixture below 10° C. will be impractical on a commercial scale owing to the special cooling equipment required and the high utility costs associated with rapidly removing heat from an exothermic reaction of this type. It would be highly desirable to develop an epoxidation process using hydrogen peroxide oxidant and organorhenium oxide catalyst which could be effectively operated at a temperature above 10° C. so as to give a product which is exclusively epoxide.

The prior art additionally teaches that it is beneficial to employ a hydrogen peroxide solution that does not contain any water and recommends the use of an organic solvent as a liquid medium for the epoxidation reaction. Suitable solvents are said to include tetrahydrofuran, monovalent aliphatic alcohols with 1-5 carbon atoms, and aromatic hydrocarbons such as toluene and xylene. Solutions in tert-butanol are taught to be especially preferred. However, hydrogen peroxide is currently available commercially only in the form of aqueous solutions. To employ one of the organic solvents recommended by the prior art, it will thus be necessary to exchange the water of a typical hydrogen peroxide solution for the organic solvent. This will necessarily increase greatly the overall costs associated with an epoxidation process of this type. Additionally, concentration of hydrogen peroxide to a pure or nearly pure state is exceedingly dangerous and is normally avoided. Thus, it will not be practicable to simply remove the water by distillation and replace it with the organic solvent. Since hydrogen peroxide has a high solubility in and high affinity for water, liquid-liquid extraction of hydrogen peroxide from an aqueous phase to an organic phase will not be feasible. Moreover, certain of the solvents taught by the prior art to be preferred for epoxidation reactions of this type such as tert-butanol are water miscible and thus could not be used in such an extraction scheme. An epoxidation process wherein a readily obtained oxidant solution is employed containing hydrogen peroxide and an organic solvent which promotes high yields of epoxide products would thus be of significant economic advantage.

SUMMARY OF THE INVENTION

This invention provides a method of epoxidizing an olefin which comprises contacting the olefin with an oxidant mixture comprised of hydrogen peroxide and an alkyl aryl secondary alcohol in the presence of an organorhenium oxide catalyst under conditions effective to epoxidize the olefin to form an epoxide. The oxidant stream may be produced by contacting the alkyl aryl secondary alcohol with molecular oxygen under conditions effective to form hydrogen peroxide.

BRIEF DESCRIPTION OF THE DRAWING

FIG. 1 illustrates in schematic form a suitable embodiment of the process of the invention.

DETAILED DESCRIPTION OF THE INVENTION

In the process of this invention, an olefin is epoxidized using hydrogen peroxide ($H_2O_2$) as an oxidizing agent. It has now been unexpectedly discovered that the yield of the desired epoxide product is greatly enhanced when an alkyl aryl secondary alcohol is employed as a component of the epoxidation reaction mixture. The rate of epoxidation (as measured by hydrogen peroxide conversion in a given period of time) and selectivity to epoxide are markedly higher than are observed under similar conditions using $C_1$–$C_5$ aliphatic alcohols taught by the prior art to be preferred solvents for this type of rhenium-catalyzed epoxidation reaction. Minimal amounts of 1,2-diol hydrolysis products are produced in the process of this invention.

The alkyl aryl secondary alcohols suitable for use include those organic compounds having at least 8 carbon atoms and corresponding to the general structure

wherein R is an aryl group and $R^1$ is an alkyl group. Most preferably, R is a $C_6$–$C_{18}$ aryl group and may be either unsubstituted (i.e., contain only hydrogen substituents other than the

substituent) or substituted with one or more keto, ester, or carboxylate group. The substituents, if any, should be selected so as to not interfere with the desired epoxidation reaction. Illustrative examples of aryl groups suitable for use as R include phenyl, methylphenyl, dimethylphenyl, trimethylphenyl, nitrophenyl, chlorophenyl, bromophenyl, cyanophenyl, methoxyphenyl, anthryl, phenanthryl, biphenyl, and the like. Preferably, however, R is phenyl ($C_6H_5$). R' is preferably a $C_1$–$C_6$ alkyl group such as methyl, ethyl, propyl, isopropyl, n-butyl, isobutyl, sec-butyl, tert-butyl, n-pentyl, isopentyl, 1-methylbutyl, 1-ethyl propyl, neopentyl, tert-pentyl, cyclopentyl, n-hexyl, isohexyl, cyclohexyl, and the like. Although heteroatom-containing substituents may be present, R' preferably contains only carbon and hydrogen. In a preferred embodiment of this invention, R is phenyl and R' is methyl (i.e., the alkyl aryl secondary alcohol is α-methyl benzyl alcohol, which is sometimes also referred to as sec-phenethyl alcohol). Other illustrative alkyl aryl secondary alcohols include 2-methylphenethyl alcohol, 3-methylphenethyl alcohol, 4-methylphenethyl alcohol, 1-phenyl-1-propanol, 1-phenyl-1-butanol, 4-chlorophenethyl alcohol, α-methyl-2-naphthalene methanol, and the like. The alkyl aryl secondary alcohol is preferably selected such that it is a liquid at the epoxidation reaction temperature and is miscible with or is capable of dissolving the other components of the reaction mixture (that is, it acts as a solvent). It is desirable that the alkyl aryl secondary alcohol have a boiling point at atmospheric pressure of from about 175° C. to 300° C.

Although the hydrogen peroxide to be utilized as the oxidizing agent may be derived from any suitable source, a distinct practical advantage of the process of this invention is that the hydrogen peroxide may be obtained by contacting the alkyl aryl secondary alcohol with molecular oxygen under conditions effective to form an oxidant stream comprised of alkyl aryl secondary alcohol and hydrogen peroxide. Typically, such an oxidant stream will also contain the ketone corresponding to the alkyl aryl secondary alcohol, minor amounts of water, and trace amounts of other active oxygen species such as organic hydroperoxides. For example, reaction of α-methyl benzyl alcohol with molecular oxygen will generally yield an oxidant stream comprised of hydrogen peroxide, acetophenone, and excess α-methyl benzyl alcohol. Crude oxidant streams obtained in this manner may be used directly in the epoxidation process of this invention to produce high yields of epoxide without the need for expensive or tedious preliminary purification or separation steps. The crude oxidant stream may contain varying amounts of substances capable of generating hydrogen peroxide under epoxidation reaction conditions. For example, hydrogen peroxide precursors such as

wherein R and R' are as described hereinabove, may be present.

Processes whereby secondary alcohols such as the alkyl aryl secondary alcohols of this invention are reacted with molecular oxygen to yield hydrogen peroxide are well known and are described, for example, in U.S. Pat. No. 2,871,102, 2,871,103, 2,871,104, 2,819,949, 2,869,989, 2,949,343, 3,003,853, 3,012,860, 3,074,782, 4,303,632, 4,897,252, 4,975,266, 5,039,508, and 5,041,680 and in British Pat. Nos. 758,907 and 758,967. The entire teachings of each of these publications are incorporated herein by reference. In a preferred embodiment, the alkyl aryl secondary alcohol is contacted with molecular oxygen in the liquid phase under conditions effective to form an oxidant stream comprised of at least about 30 weight percent alkyl aryl secondary alcohol, the ketone resulting from reduction of the alkyl aryl secondary alcohol, from about 1 to 10 weight percent hydrogen peroxide, and water. Said contacting is most preferably carried out under the conditions described in U.S. Pat. Nos. 4,897,252, 4,975,266, and 5,039,508.

Although any organorhenium oxide compound which is active as an epoxide catalyst for the hydrogen peroxide oxidation of an olefin may be employed in the process of this invention, the compounds described in DE 3,902,357 or the United States equivalent thereof and in Herrmann, *J. Organomet. Chem.* 382, 1(1990) are particularly preferred for use. These publications are incorporated herein by reference in their entirety.

One class of suitable organorhenium oxide catalysts includes compounds having the general formula

wherein a is 1–6, b is 1–14, Re has a valence of from 5–7, and $R^1$ is alkyl or aralkyl. Preferably, c is not greater than 3·b. The $R^1$ groups may be the same or different and are preferably $C_1$–$C_{10}$ alkyl (methyl, ethyl, propyl, isopropyl, n-butyl, isobutyl, sec-butyl, tert-butyl, n-pentyl, isopentyl, 1-methylbutyl, 1-ethylpropyl, neopentyl, tert-pentyl, cyclopentyl, n-hexyl, isohexyl, cyclohexyl, $C_7H_{15}$ isomers, $C_8H_{17}$ isomers, $C_9H_{19}$ isomers, $C_{10}H_{21}$ isomers, and the like) or $C_7$–$C_9$ aralkyl (benzyl, phenthyl, and the like). Substituted $R^1$ groups may also be utilized; halogenated $R^1$ groups are especially useful. To minimize steric hindrance of the desired epoxidation reaction, catalysts of this type preferably contain no more than three groups with more than 6 carbons per rhenium atom. At least one hydrogen atom is preferably bonded to the alpha carbon of each $R^1$ group. Illustrative organorhenium oxide catalysts of this type tetramethyl tetraoxodirhenium (VI), ethyl rhenium trioxide, n-propyl rhenium trioxide, cyclohexyl rhenium trioxide, n-butyl rhenium trioxide, benzyl rhenium trioxide, tetraethyl tetraoxodirhenium (VI), and the like. Methods of preparing such compounds are well known and are described, for example, in DE 3,902,357 (Herrmann, *J. Organomet. Chem.* 382, 1(1990), Herrmann, *Angew. Chem.* 100, 420(1988), and DE 3,841,733; these publications are incorporated herein by reference in their entirety. This class of catalysts also include the polymeric organorhenium oxides of the type taught in Herrmann, et al., *Angew. Chem. Int. Ed. Eng.* 30, 1638(1991), incorporated herein by reference, and having the approximate empirical formula $[R^1ReO_3]_x$.

Also appropriate for use as catalysts in the process of this invention are ligand-containing organorhenium oxide compounds having the general formula

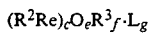(R²Re)$_d$O$_e$R³$_f$·L$_g$ wherein d is 1 or 2, e is an integer of from 1 to 3·d, f is 0 or an integer of from 1 to 2·d, g is an integer of from 1 to 3·d, Re has a valence of 5 to 7, R² is alkyl or aralkyl, R³ is alkyl, aralkyl, or aryl, and L is a ligand containing 1 to 3 heteroatoms selected from O and N and coordinated to Re. The R² groups may be the same or different and are preferably substituted or unsubstituted $C_1$–$C_{10}$ alkyl or $C_7$–$C_9$ aralkyl. Any of the organic radicals taught herein above to be suitable for use as R¹ may also be employed as R². R³ is preferably a $C_1$–$C_{10}$ alkyl, $C_7$–$C_9$ aralkyl, or $C_6$–$C_{10}$ aryl group. R² and R³ may be the same or different. Preferred $C_6$–$C_{10}$ aryl groups include phenyl, tolyl, xylyl, mesityl, halophenyl, nitrophenyl, cyanophenyl, and alkoxyphenyl. Catalysts of this type differ from those described hereinabove in that they contain at least one heteratom-containing ligand. Suitable ligands include, but are not limited to, ammonia, primary amines (H₂NR), secondary amines (HNR₂), or tertiary amines (NR₂) where R is a branched or unbranched alkyl, aralkyl, or aryl group, aromatic azacycles such as pyridine and its ring substituted and anellated derivatives such as 8-hydroxyquinoline, O,O'-, N,O-, or N,N'- chelate ligands such as 2,2'-bipyridine, 2-aminopyridine, 2-(aminomethyl)pyridine, substituted piperazines, amino-substituted piperidine or pyrrolidines, alkoxy-substituted pyridines such as methoxy pyridine, 1,3-diketones such as acetyl acetone, 1,2-diketones such as diacetyl or 2,3-pentanediol, β-aminoalcohols such as 2-aminoethanol, 2-aminophenol, 2-amino-1-butaniol, or ephedrine, β-aminoaldehydes, β-aminoketones, 1,2-diimides, β-aminoethers such as 2-(aminomethyl) tetrahydrofuran, aromatic N-oxides such as 2,2'-bipyridine N,N-dioxide or pyridine N-oxide, 1,2-diamines such as ethylene diamine, or hydroxy carboxylic acids such as tartaric acid and its esters. Other illustrative ligands include quinuclidine, aniline, triethylamine, 1,4-diazabicyclo[2.2.2]octane, methoxyaniline, 2-(aminomethyl) pyridine, 2-(aminoethyl)pyridine, (N,N-dimethylamino) acetonitrile, (N,N-dimethylamino)acetone, and the like. Tertiary amines, tertiary amine oxides, aromatic azacycles (e.g., pyridine), and aromatic azacycle oxides (e.g., pyridine-N-oxide) are the classes of ligands generally preferred for use. The ligand may be mono-, bi-, tri-, or polydentate (i.e., contain one or more coordinating heteroatoms) and may contain or be coordinately bonded to metals other than rhenium. Ligand-containing organorhenium oxide compounds of this type are well known in the art and are described, for example, in the German patents and Herrmann papers listed hereinabove. It has now been unexpectedly discovered that the use of such catalysts is advantageous in that this class of organorhenium oxide catalysts tends to produce the lowest levels of undesired 1,2-diol hydrolysis by-products.

Also suitable for use in the process of this invention are polymer-bound organorhenium oxide catalysts having the general structure (polymer)$_h$·(R⁴$_i$Re$_j$O$_k$)$_l$ wherein the polymer has ligand sites containing 1 to 3 heteroatoms selected from O and N and coordinated to Re, the ratio

$\frac{1}{h}$ represents the molar ratio of

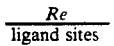$\frac{Re}{\text{ligand sites}}$ and is from 0.01 to 10, i is an integer of from 1 to 6, j is an integer of from 1 to 4, k is an integer of from 1 to 14, Re has a valence of from 5 to 7, and R⁴ is alkyl or aralkyl. Most preferably, the ligand sites comprise amine nitrogen or amide nitrogen. R⁴ may be any of the organic radicals described hereinabove as appropriate for use as R¹. Suitable heteroatom-containing polymers include, for example, poly-4-vinyl pyridine, poly-2vinyl pyridine, poly-2-vinyl pyridine co-styrene, poly(acrylic acid amide), polyvinyl pyrrolidone, polyimide, polyamides such as nylon 6, as well as the various ion exchange resins containing amine groups. German Pat. No. 3,902,357 describes methods for obtaining suitable polymer-bound organorhenium oxide catalysts. An advantage of using this type of organorhenium oxide catalyst is that the catalyst may be easily recovered from the epoxidation reaction mixture by filtration and used again in subsequent epoxidations. Another advantage is that such catalysts generally give high selectivity to epoxide.

The amount of catalyst employed is not critical, but should be sufficient so as to substantially accomplish the desired epoxidation reaction in a practicably short period of time. The optimum quantity of catalyst will depend upon a number of factors including reaction temperature, olefin reactivity and concentration, hydrogen peroxide concentration, type and concentration of alkyl aryl secondary alcohol and catalyst activity. Typically, however, the molar ratio of Re in the organorhenium oxide catalyst to hydrogen peroxide (Re:H₂O₂) will be from about 0.01:100 to 1:100. The weight concentration of the catalyst in the epoxidation reaction mixture will generally be from about 0.01 to 1.0 percent.

The olefin substrate epoxidized in the process of this invention may be any organic compound having at least one ethylenically unsaturated functional group (i.e., a carbon-carbon double bond) and may be an aromatic, aliphatic, mixed aromatic-aliphatic (e.g., aralkyl), cyclic, branched or straight chain olefin. Preferably, the olefin contains from 2 to 30 carbon atoms (i.e., a $C_2$–$C_{30}$ olefin). More than one carbon-carbon double bond may be present in the olefin; dienes, trienes, and other polyunsaturated substrates thus may be used. Other examples of suitable substrates include unsaturated fatty acids or fatty acid derivatives such as esters or glycerides and oligomeric or polymeric unsaturated compounds such as polybutadiene.

The olefin may contain substituents other than hydrocarbon substituents such as halide, carboxylic acid, ether, hydroxy, thiol, nitro, cyano, ketone, ester, anhydride, amino, and the like.

Exemplary olefins suitable for use in the process of this invention include ethylene, propylene, the butenes, butadiene, the pentenes, isoprene, 1-hexene, 3-hexene, 1-heptene, 1-octene, diisobutylene, 1-nonene, 1-tetradecene, pentamyrcene, camphene, 1-undecene, 1-dodecene, 1-tridecene, 1-tetradecene, 1-pentadecene, 1-hexadecene, 1-heptadecene decene, 1-nonadecene, 1-eicosene, the trimers and tetramers of propylene, polybutadiene, polyisoprene, cyclopentene, cyclohexene, cycloheptene, cyclooctene, cyclooctadiene, cyclododecene, cyclododecatriene, dicyclopentadiene, methylenecyclopropane, methylenecyclopentane, methylenecyclohexane, vinylcyclohexane, vinyl cyclohexene, methallyl ketone, allyl chloride, allyl bromide, acrylic acid, methacrylic acid, crotonic acid, vinyl acetic acid, crotyl chloride, methallyl chloride, the dichlorobutenes, allyl alcohol, allyl carbonate, allyl acetate, alkyl acrylates and methacrylates, diallyl maleate, diallyl phthalate, unsaturated triglycerides such as soybean oil, and unsaturated fatty acids, such as oleic acid, linolenic acid, linoleic acid, erucic acid, palmitoleic acid, and ricinoleic acid and their esters (including mono-, di-, and triglyceride esters), and alkenyl aromatic compounds such as styrene, α-methyl styrene, β-methyl styrene, divinyl benzene, 1,2-dihydronaphthalene, indene, stilbene, cinnamyl alcohol, 2-methyl-1-phenyl-1-propene, 2-methyl-3-phenyl-2-propen-1-ol, cinnamyl acetate, cinnamyl bromide, cinnamyl chloride, 4-stilbenemethanol, ar-methyl styrene, ar-ethyl styrene, ar-tert-butyl styrene, archlorostyrene, 1,1-diphenylethylene, vinyl benzyl chloride, vinyl naphthalene, vinyl benzoic acid, ar-acetoxy styrene, ar-hydroxy styrene (i.e., vinyl phenol), 2- or 3-methyl indene, 2,4,6-trimethylstyrene, 1-phenyl-1-cyclohexene, 1,3-diisopropenyl benzene, vinyl anthracene, vinyl anisole, and the like.

Mixtures of olefins may be epoxidized and the resulting mixture of epoxides either employed in mixed form or separated into the different component epoxides.

The process of this invention is especially useful for the epoxidation of $C_2-C_{30}$ olefins having the general structure

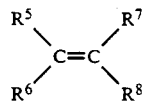

wherein $R^5$, $R^6$, $R^7$, and $R^8$ are the same or different and are selected from the group consisting of hydrogen, $C_1-C_6$ alkyl (linear, branched, or cyclic), $C_6-C_{15}$ aryl, and $C_7-C_{20}$ aralkyl.

The amount of hydrogen peroxide relative to the amount of olefin is not critical, but most suitably the molar ratio of hydrogen peroxide:olefin is from about 100:1 to 1:100 when the olefin contains one ethylenically unsaturated group. The molar ratio of ethylenically unsaturated groups in the olefin substrate to hydrogen peroxide is more preferably in the range of from 1:10 to 10:1. One equivalent of hydrogen peroxide is theoretically required to oxidize one equivalent of a mono-unsaturated olefin substrate, but it may be desirable to employ an excess of one reactant to optimize selectivity to the epoxide. A key advantage of the process of this invention is that a large molar excess of hydrogen peroxide relative to olefin is not required. High yields of epoxide may be realized using a slight (i.e., 5-25%) molar excess of olefin relative to hydrogen peroxide. The hydrogen peroxide is thus used in a very efficient manner; little of the hydrogen peroxide is wasted through non-selective decomposition to water (i.e., without oxidation of an olefin molecule). Since the hydrogen peroxide is relatively costly to generate, this means that the overall integrated process of the invention may be economically practiced on a commercial scale.

The reaction temperature is not critical, but should be sufficient to accomplish substantial conversion of the olefin to epoxide within a reasonably short period of time. It is generally advantageous to carry out the reaction to achieve as high a hydrogen peroxide conversion as possible, preferably at least 50% and desirably at least 90%, consistent with reasonable selectivities. The optimum reaction temperature will be influenced by catalyst activity, olefin reactivity, reactant concentrations, and type of alkyl aryl secondary alcohol employed, among other factors, but typically will be in a range of from about −30° C. to 100° C. When using methyl rhenium oxide or an amine ligand-containing methyl rhenium oxide as catalyst, the temperature will more preferably be from about 20° C. to 60° C. Since the epoxidation reaction tends to be exothermic, it may be desirable to employ a means of removing heat from the reaction mixture. Reaction times of from about 10 minutes to 48 hours will typically be appropriate, depending upon the above-identified variables. Although sub-atmospheric pressures can be employed, the reaction is preferably performed at atmospheric pressure or at elevated pressure (typically, not greater than about 2,000 psig). Generally, it will be desirable to maintain the reaction components as a liquid phase mixture.

The process of this invention may be carried out in a batch, continuous, or semi-continuous manner using any appropriate type of reaction vessel or apparatus. Known methods for conducting metal catalyzed epoxidations of olefins using hydrogen peroxide will generally also be suitable for use in this process. Thus, the reactants may be combined all at once or sequentially. For example, the hydrogen peroxide may be added incrementally to the reaction zone. Once the epoxidation has been carried out to the desired degree of conversion, the desired epoxide product may be separated and recovered from the reaction mixture using any appropriate technique such as fractional distillation, extractive distillation, liquid-liquid extraction, crystallization, or the like. After separating from the epoxidation reaction mixture, the recovered organorhenium oxide catalyst (which may be either homogeneous or heterogeneous) may be economically re-used in subsequent epoxidations. Similarly, any unreacted olefin or hydrogen peroxide may be separated and recycled. The crude epoxidation reaction mixture will also contain the alkyl aryl secondary alcohol and, generally, the corresponding alkyl aryl ketone produced in an initial step wherein the alcohol is reacted with molecular oxygen to form hydrogen peroxide. After separation of the epoxide from the alkyl aryl secondary alcohol and the alkyl aryl ketone, the ketone may be converted back to alkyl aryl secondary alcohol by hydrogenation. For example, the ketone may be reacted with hydrogen in the presence of a transition metal hydrogenation catalyst. Hydrogenation reactions of this type are well known to those skilled in the art. The alkyl aryl secondary alcohol may also be dehydrated using known methods to yield valuable alkenyl aromatic products such as styrene.

FIG. 1 illustrates one embodiment of the integrated epoxidation process of this invention wherein a relatively light olefin such as propylene is epoxidized to yield a volatile epoxide. A stream comprised of alkyl aryl secondary alcohol passes via line 21 into alcohol oxidation zone 1 wherein the alkyl aryl secondary alcohol is reacted with molecular oxygen to form an oxidant stream comprised of hydrogen peroxide, alkyl aryl ketone, and excess alkyl aryl secondary alcohol. The molecular oxygen is provided by air introduced via line 2.

Conditions of temperature and pressure and the rates of addition and concentration of the reactants are preferably maintained in zone 1 effective to maintain the oxygen absorption rate in the liquid phase at 90% or more of the maximum oxygen absorption rate. The water content of the reaction mixture is desirably maintained below 4 wt. %, preferably below 2 wt. % and most preferably below 1 wt. % by stripping water formed during the oxidation out of the reaction mixture with unreacted oxygen and/or inert gases via line 3A. Preferably, the oxygen partial pressure in these gases is regulated at a value not more than 3.0, preferably not more than 2.0, times the minimum value at the maximum oxygen absorption rate.

In especially preferred practice, reaction zone 1 is comprised of a plurality of separate reaction zones. The liquid reaction mixture is passed in series from one zone to the next while the oxygen-containing gas is introduced in parallel to each of the reaction zones. Each zone is thoroughly back-mixed. Hydrogen peroxide concentration is lowest in the first zone and increases in each successive zone, reaching a maximum in the final zone.

The oxidant stream containing hydrogen peroxide passes from zone 1 via line 3 and may be used directly as the source of oxidant in the olefin epoxidation reaction which takes place in olefin epoxidation zone 4. Alternatively, the oxidant stream may be further processed or purified prior to introduction into zone 4.

The olefin to be epoxidized is fed into zone 4 via line 6, while the organorhenium oxide catalyst is introduced via line 5. The resulting reaction mixture is maintained at the desired temperature and pressure in zone 4 for a time sufficient to convert at least a portion, and preferably at least about 50% of the olefin to epoxide, thereby consuming a portion of the hydrogen peroxide (preferably, substantially all of the hydrogen peroxide is consumed). The crude epoxidation product thus obtained passes through line 7 to epoxide purification zone 8 where it is separated by fractional distillation or other such means into a recycled olefin stream (returned to olefin feed line 6 or olefin epoxidation zone 4 via line 9), a lights stream containing water and/or organics having a boiling point less than that of the epoxide (withdrawn via line 10), an epoxide stream containing the desired epoxide product (withdrawn via line 11), and an ketone-/alcohol stream comprised of the secondary alkyl aryl alcohol and alkyl aryl ketone (withdrawn via line 13). If unreacted hydrogen peroxide is present, it may either be removed in the form of an aqueous or organic solution or decomposed by some suitable method. If desired, a heavies stream containing organic compounds having boiling points higher than that of the alcohol and ketone as well as the organorhenium oxide catalyst may be separated and withdrawn via line 12. The organorhenium oxide catalyst may be recovered from this stream and returned to the olefin epoxidation zone via line 5.

Optionally, further purification of the ketone/alcohol stream may be carried out in ketone/alcohol purification zone 14 by any suitable means such as distillation, countercurrent extraction, or the like. Certain compounds such as phenols may be present in the ketone/alcohol stream which may tend to inhibit the molecular oxygen oxidation of the secondary alkyl aryl alcohol to hydrogen peroxide and alkyl aryl ketone. It is therefore desirable to treat this stream in zone 14 to remove such compounds or to convert them into non-inhibitive compounds. Preferably, zone 14 comprises both distillation and caustic and/or ion exchange treatment means. Additional heavies may be withdrawn via line 15 and make-up secondary alkyl aryl alcohol introduced via line 16 as necessary. The purified ketone/alcohol stream is passed via line 17 to hydrogenation zone 18 wherein the stream is reacted with hydrogen (introduced via line 19) in the presence of a suitable hydrogenation catalyst such as a supported platinum or palladium catalyst (introduced via line 20) so as to convert at least a portion, and preferably substantially all, of the alkyl aryl ketone generated in alcohol oxidation zone 1 back to alkyl aryl secondary alcohol. The hydrogenated stream produced in zone 18 is passed via line 21 to alcohol oxidation zone 1. This integrated process is preferably operated in a continuous manner such that the desired epoxide is the only major organic product and the alkyl aryl ketone is recycled.

From the foregoing description, one skilled in the art can readily ascertain the essential characteristics of this invention, and, without departing from the spirit and scope thereof, can make various changes and modifications of the invention to adapt it to various usages, conditions, and embodiments.

The following examples further illustrate the process of this invention, but are not limitative of the invention in any manner whatsoever.

EXAMPLE 1

This example demonstrates that propylene may be epoxidized in high yield using the process of this invention. An oxidant stream was prepared by stirring a mixture of $\alpha$-methyl benzyl alcohol (70 mL), acetophenone (30 mL), and 50% aqueous hydrogen peroxide (0.15 mole $H_2O_2$) with magnesium sulfate (30 g) for 30 minutes. After filtration, the oxidant stream contained about 5% hydrogen peroxide and 1% water. Methyl rhenium trioxide catalyst (0.20 g; 0.53 mole %; 0.80 mmole) and pyridine (0.075 mL; 0.93 mmole) were then added to yield a yellow solution.

The solution was transferred to a glass-line autoclave equipped with a teflon stir blade, thermowell, and propylene inlet line. The reactor was charged with propylene (16 mL; 0.20 mole). Over a two hour reaction time, the temperature of the stirred mixture rose from 19° C. to 30° C. (no external heating or cooling was supplied) and the pressure dropped 50–60 psig. The reactor was cooled with an external ice bath and then vented into a gas bag. The contents of the gas bag and the liquid phase withdrawn from the reactor were then analyzed by gas chromatography. An 82% conversion of the hydrogen peroxide was observed, with 80% selectivity to propylene oxide (based on $H_2O_2$). No by-products derived from propylene were detected.

EXAMPLE 2–7

Example 1 was repeated, but with the following changes in reaction conditions. Molecular sieves were added to the epoxidation reaction mixture in Example 2. The reaction time in Example 3 was 4 hours instead of 2 hours. Example 4 employed 0.3 mole % catalyst, while Example 5 used 0.9 mole % catalyst. In Example 6, the oxidant stream was obtained by molecular oxygen C oxidation of α-methyl benzyl alcohol and contained ca. 70% α-methyl benzyl alcohol, 25% acetophenone, 5% hydrogen peroxide, and 1% water. In Example 7, no pyridine was added. The results obtained in these Examples are summarized in Table I.

TABLE I

| Example | Temp. Range (°C.) | $H_2O_2$ Conversion | Selectivity to Epoxide |
|---|---|---|---|
| 2 | 14–27 | 74 | 53 |
| 3 | 17–31 | 95 | 65 |
| 4 | 15–31 | 59 | 65 |
| 5 | 16–32 | 97 | 60 |
| 6 | 23–30 | 90 | 67 |
| 7 | 19–31 | 89 | 41[a] |

[a]propylene glycol

EXAMPLES 8–14

The procedure of Example 1 was repeated with an external heating coil being attached to the autoclave reactor to study the effect of temperature on conversion and selectivity. The autoclave was still charged at ambient temperature, but the external coil was heated to 32° C. The results obtained are summarized in Table II. The column headed "Temperature" gives the initial and maximum temperatures observed for each reaction mixture.

TABLE II

| Example | Temp. Range (°C.) | $H_2O_2$ Conversion | Selectivity to Epoxide |
|---|---|---|---|
| 8 | 21–38 | 95 | 89 |
| 9 | 27–41 | 92 | 80 |
| 10 | 23–39 | 89 | 79 |
| 11 | 24–47 | 92 | 84 |
| 12 | 26–50 | 86 | 83 |
| 13 | 45–55 | 96 | 45 (15 PG[a]) |
| 14 | 14=8– | 98 | 0[b] |

[a]propylene glycol
[b]17% styrene, 18% styrene oxide

These results show that consistently high selectivities to epoxide may be obtained using the process of the invention. As the reaction temperature exceeds about 60° C., however, non-selective decomposition of the hydrogen peroxide (to oxygen and water) begins to compete with epoxidation. High selectivity to epoxide at relatively high reaction temperatures may be accomplished by either more careful control of the initial exotherm, slow addition of olefin to the reaction mixture, or the use of other organorhenium oxide catalysts.

EXAMPLES 15–19

These examples illustrate the use of coordinating ligands other than pyridine. The procedure of Example 1 was repeated with the exception that an external heating coil maintained at 32° C. was employed and the olefin was slowly added through a metering valve to the mixture of the oxidant stream and catalyst. Examples 16 and 18 used a crude oxidant stream obtained by molecular oxygen oxidation of α-methyl benzyl alcohol having a composition similar to that used in Example 6. The results observed in these runs are provided in Table III.

TABLE III

| Example | Ligand | Temperature (°C.) | $H_2O_2$ Conversion | Selectivity to Epoxide |
|---|---|---|---|---|
| 15 | pyridine | 27–42 | 88 | 92 |
| 16 | pyridine | 28–42 | 91 | 91 |
| 17 | pyridine N-oxide | 27–40 | 85 | 88 |
| 18 | pyridine N-oxide | 27–39 | 88 | 90 |
| 19 | methyl morpholine N-oxide | 27–37 | 79 | 83 |

EXAMPLE 20–26

These examples demonstrate that the use of a alkyl aryl secondary alcohol in the process of this invention provides higher yields of epoxide product as compared to other alcohol solvents. The procedure of Example 9 was repeated except for the substitution of the solvents shown in Table IV for the α-methylbenzyl alcohol/acetophenone mixture.

TABLE IV

| Example | Solvent | $H_2O_2$ Conversion | Epoxide Selectivity, % | Epoxide Yield, % |
|---|---|---|---|---|
| 20 | α-methylbenzyl alcohol | 92 | 82 | 75 |
| *21 | isopropanol/acetone | 31 | 39 | 12 |
| *22 | isopropanol/acetone[a] | 47 | 49 | 23 |
| *23 | cyclohexanol/cyclohexanone | 19 | 24 | 5 |
| *24 | acetophenone | 53 | 81 | 43 |
| *25 | benzyl alcohol | 82 | 73 | 60 |
| *26 | t-butyl alcohol | 62 | 89 | 55 |

*comparative example
[a]1.0 mole % catalyst

A 75% yield of propylene oxide based on hydrogen peroxide was obtained using an alkyl aryl secondary alcohol as solvent (Example 20). Both hydrogen peroxide conversion and epoxide selectively decreased substantially when dialkyl secondary alcohol/ketone mixtures were utilized (Examples 21–23). While acetophenone and t-butyl alcohol (Examples 24 and 26) gave epoxide selectivities comparable to that observed for α-methyl benzyl alcohol, the rate of reaction was considerably slower as reflected in the decreased hydrogen peroxide conversion. The overall yield of epoxide for a given reaction time thus was decreased with these solvents as compared to the alkyl aryl secondary alcohol solvent of Example 20.

We claim:

1. A method of epoxidizing an olefin which comprises contacting the olefin with an oxidant mixture comprised of hydrogen peroxide and an alkyl aryl secondary alcohol in the presence of an organorhenium oxide catalyst under conditions effective to epoxidize the olefin to form an epoxide.

2. The method of claim 1 wherein the alkyl aryl secondary alcohol is α-methyl benzyl alcohol.

3. The method of claim 1 wherein said oxidant mixture is produced by contacting the alkyl aryl secondary alcohol with molecular oxygen.

4. The method of claim 1 wherein said olefin is a $C_2$–$C_{30}$ olefin.

5. The method of claim 1 wherein the organorhenium oxide catalyst is selected from the group consisting of:
 (a) compounds having the general formula $$R^1{}_a Re_b O_c$$

wherein a is 1-6, b is 1-4, c is 1-14, Re has a valance of from 5-7, and $R^1$ is alkyl or aralkyl;
(b) compounds having the general formula $$(R^2Re)_d O_e R^3{}_f \cdot L_g$$

wherein d is 1 or 2, e is an integer of from 1 to 3·d, f is 0 or an integer of from 1 to 2·d, g is an integer of from 1 to 3·d, Re has a valance of 5 to 7, $R^2$ is alkyl or aralkyl, $R^3$ is alkyl, aralkyl, or aryl, and L is an ligand containging 1 to 3 heteroatoms selected from O and N and coordinated to Re;
(c) substances having the general formula $$(polymer)_h \cdot (R^4{}_i Re_j O_k)_l$$

wherein the polymer has ligand sites containing 1 to 3 heteroatoms selected from O and N and coordinated to Re, the ratio $$\frac{1}{h}$$

represents the molar ratio of $$\frac{Re}{\text{ligand sites}}$$

and is from 0.01 to 10, i is an integer of from 1 to 6, j is an integer of from 1 to 4, k is an integer of from 1 to 14, Re has a valence of from 5 to 7, and $R^4$ is alkyl or aralkyl; and
(d) mixtures thereof.

6. The method of claim 1 wherein the oxidant mixture additionally comprises an alkyl aryl ketone.

7. The method of claim 1 wherein the oxidant mixture additionally comprises water.

8. The method of claim 1 wherein said contacting is carried out at a temperature in the range of from about $-30°$ C. to 100° C.

9. The method of claim 1 wherein the concentration of hydrogen peroxide in said oxidant mixture is from about 1 to 10 weight percent.

10. The method of claim 1 wherein the concentration of alkyl aryl secondary alcohol in said oxidant mixture is at least about 30 weight percent.

11. The method of claim 1 wherein the molar ratio of hydrogen peroxide to olefin is from about 1:10 to 10:1.

12. The method of claim 1 wherein the molar ratio of Re in the organorhenium oxide catalyst to hydrogen peroxide is from about 0.01:100 to 1:100.

13. A method of epoxidizing a $C_2$-$C_{30}$ olefin which comprises contacting the olefin with an oxidant mixture comprised of hydrogen peroxide, methyl benzyl alcohol, acetophenone, and water in the presence of an organorhenium oxide catalyst having the general formula $$(R^2Re)_d O_e R^3{}_f \cdot L_g$$

wherein d is 1 or 2, e is an integer of from 1 to 3 d, f is 0 or an integer of from 1 to 2·d, g is an integer of from 1 to 3·d, Re has a valence of 5 to 7, $R^2$ is alkyl or aralkyl, $R^3$ is alkyl, aralkyl, or aryl, and L is a ligand containing 1 to 3 heteroatoms selected from O and N and coordinated to Re at a temperature of from about 31 30° C. to 100° C. to form an epoxide, the concentration of hydrogen peroxide in said oxidant mixture being from about 1 to 10 weight percent, the concentration of methyl benzyl alcohol in said oxidant mixture being at least about 30 weight percent, the molar ratio of hydrogen peroxide:olefin is from about 1:10 to 10:1, and the molar ratio of Re in the organorhenium oxide catalyst to hydrogen peroxide is from about 0.01:100 to 1:100.

14. The method of claim 13 wherein the $C_2$-$C_{30}$ olefin has the general structure

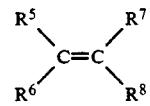

wherein $R^5$, $R^6$, $R^7$, and $R^8$ are the same or different and are selected from the group consisting of hydrogen, $C_1$-$C_6$ alkyl, $C_6$-$C_{15}$ aryl, and $C_7$-$C_{20}$ aralkyl.

15. The method of claim 13 wherein the $C_2$-$C_{30}$ olefin is selected from the group consisting of ethylene, propylene, isobutylene, 2-butene, 1-butene, allyl alcohol, cyclohexene, allyl chloride, styrene, 1-octene, butadiene, 1-pentene, 2-pentene, 2,3-dimethyl-2-butene, 2-methyl-1-pentene, 2-methyl-2-butene, cyclooctene, stilbene, phenyl allyl ether, $\alpha$-methyl sytrene, methallyl alcohol, 1-decene, 1-dodecene, 1-hexadecene, 1-hexene, methyl allyl ether, and norbornene.

16. The method of claim 13 wherein $R^2$ is methyl, d is 1, e is 3, and f is 0.

17. The method of claim 13 wherein the ligand is selected from the group consisting of tertiary amines, tertiary amine oxides, aromatic azacycles, and aromatic azacycle oxides.

18. The method of claim 13 wherein the ligand is selected from the group consisting of pyridine and pyridine N-oxide.

19. An integrated process for the production of an epoxide comprising the steps of
(a) contacting an alkyl aryl secondary alcohol with molecular oxygen under conditions effective to form an oxidant mixture comprised of the alkyl aryl secondary alcohol, an alkyl aryl ketone, and hydrogen peroxide; and
(b) contacting the oxidant mixture with an olefin and an organorhenium oxide catalyst under conditions effective to epoxidize the olefin to form an epoxide.

20. The method of claim 19 comprising the additional step of separating the epoxide from the alkyl aryl secondary alcohol and the alkyl aryl ketone.

21. The method of claim 20 comprising the additional step of reacting the alkyl aryl ketone with hydrogen in the presence of a transition metal hydrogenation catalyst under conditions effective to convert the alkyl aryl ketone to the alkyl aryl secondary alcohol.

22. The method of claim 19 wherein the alkyl aryl secondary alcohol is $\alpha$-methyl benzyl alcohol.

23. The method of claim 19 wherein step (a) is carried out in the liquid phase.

24. The method of claim 19 wherein the concentration of hydrogen peroxide in the oxidant stream is from about 1 to 10 weight percent.

25. An integrated process for the production of an epoxide comprising the steps of
(a) contacting $\alpha$-methyl benzyl alcohol with molecular oxygen in the liquid phase under conditions effective to form an oxidant mixture comprised of at least about 30 weight percent $\alpha$-methyl benzyl alcohol, acetophenone, from about 1 to 10 weight percent hydrogen peroxide, and water;

(b) contacting the oxidant mixture with a $C_2$–$C_{30}$ olefin and an organorhenium oxide catalyst having the general formula $$(R^2Re)_dO_eR^3_f \cdot L_g$$

wherein d is 1 or 2, e is an integer of from 1 to 3·d, f is 0 or an integer of from 1 ti 2·d, g is an integer of from 1 to 3·d, Re has a valence of from 5 to 7, $R^2$ is alkyl or aralkyl, $R^3$ is alkyl, aralkyl, or aryl, and L is a ligand containing from 1 to 3 heteroatoms selected from O and N and coordinated to Re at a temperature of from about $-30°$ C. to $100°$ C. to form an epoxide, the molar ratio of hydrogen peroxide:olefin being from about 1:10 ti 10:1, and the molar ratio of Re in the organorhenium oxide catalyst to hydrogen peroxide being from about 0.01:100 to 1:100;

(c) separating the epoxide form the α-methyl benzyl alcohol and acetophenone; and (d) reacting the acetophenone with hydrogen in the presence of a transition metal hydrogenation catalyst to convert the acetophenone to α-methyl benzyl alcohol.

26. The method of claim 25 wherein the $C_2$14 $C_{30}$ olefin is propylene.

27. The method of claim 25 wherein the organorhenium oxide catalyst has a methyl group attached to Re.

28. The method of claim 25 wherein L is selected from the group consisting of tertiary amines, tertiary amine oxides, aromatic azacycles, and aromatic azacycle oxides.

29. The method of claim 25 wherein the temperature is from about $20°$ C. to $60°$ C.